(12) United States Patent
Lee (10) Patent No.: US 11,931,129 B2
(45) Date of Patent: Mar. 19, 2024

(54) SMART THERMOMETER AND METHOD FOR MEASURING BODY TEMPERATURE USING THE SAME

(71) Applicant: Littleone Inc., Seongnam-si (KR)

(72) Inventor: Byung Kyu Lee, Seoul (KR)

(73) Assignee: LITTLEONE INC., Seongnam-si (KR)

( * ) Notice: Subject to any disclaimer, the term of this patent is extended or adjusted under 35 U.S.C. 154(b) by 474 days.

(21) Appl. No.: 17/084,695

(22) Filed: Oct. 30, 2020

(65) Prior Publication Data

US 2022/0133153 A1 May 5, 2022

(30) Foreign Application Priority Data

Oct. 29, 2020 (KR) .................. 10-2020-0141895

(51) Int. Cl.
*G01K 13/00* (2021.01)
*A61B 5/00* (2006.01)
*A61B 5/01* (2006.01)

(52) U.S. Cl.
CPC .............. *A61B 5/01* (2013.01); *A61B 5/0008* (2013.01); *A61B 5/742* (2013.01); *A61B 5/746* (2013.01);
(Continued)

(58) Field of Classification Search
CPC ........... A61B 5/01; A61B 5/008; A61B 5/742; A61B 5/746; A61B 2562/0271
See application file for complete search history.

(56) References Cited

U.S. PATENT DOCUMENTS 4,065,758 A * 12/1977 Barbier .................. G08B 17/06
340/870.18
6,629,776 B2 * 10/2003 Bell ....................... G01K 7/245
374/170
(Continued)

FOREIGN PATENT DOCUMENTS

KR 10-2011-0054567 A 5/2011
KR 10-2014-0116579 A 10/2014
(Continued)

OTHER PUBLICATIONS

17084695_2023-11-02_KR_20190033753_A_H.pdf.Apr. 2019.*
17084695_2023-11-02_KR_20170142701_A_H.pdf, Dec. 2017.*

*Primary Examiner* — Gail Kaplan Verbitsky
(74) *Attorney, Agent, or Firm* — INVENSTONE PATENT, LLC.

(57) ABSTRACT

A smart thermometer and a method for measuring body temperature using the same are provided. The method for measuring body temperature using a smart thermometer comprises: performing advertising in idle mode; switching the smart thermometer to active mode and connecting to user equipment; measuring body temperature by using a temperature sensor; determining whether the measured body temperature stays below a first threshold for a preset period of time; if the measured body temperature stays below the first threshold for a preset period of time, switching to idle mode and performing advertising; and if the measured body temperature reaches or exceeds the first threshold within the preset period of time, displaying the measured body temperature on a display window and transmitting the measured body temperature to the user equipment.

12 Claims, 6 Drawing Sheets

(52) U.S. Cl.
CPC ...... *A61B 2562/0271* (2013.01); *G01K 13/00* (2013.01)

(56) References Cited

U.S. PATENT DOCUMENTS

| | | | | |
|---|---|---|---|---|
| 8,328,420 B2 * | 12/2012 | Abreu | ................ | A61B 5/6898 |
| | | | | 374/170 |
| 8,808,178 B2 * | 8/2014 | Lane | ................ | A61B 5/01 |
| | | | | 600/323 |
| 8,958,853 B1 * | 2/2015 | Bovis | ................ | G06F 3/048 |
| | | | | 455/569.2 |
| 8,981,926 B2 * | 3/2015 | Al-Ali | ................ | G08B 21/0211 |
| | | | | 340/539.12 |
| 9,019,106 B2 * | 4/2015 | Alameh | ................ | G04G 21/02 |
| | | | | 340/573.5 |
| 9,602,954 B2 * | 3/2017 | Youn | ................ | H04W 8/005 |
| 9,723,986 B1 * | 8/2017 | Mullin | ................ | A61B 5/002 |
| 9,809,228 B2 * | 11/2017 | Hong | ................ | B60W 50/14 |
| 10,154,399 B2 * | 12/2018 | Gaurav | ................ | H04M 1/72412 |
| 10,222,276 B2 * | 3/2019 | Yoon | ................ | G01J 1/0219 |
| 10,479,979 B2 * | 11/2019 | Keidar | ................ | C12N 5/0693 |
| 10,847,016 B1 * | 11/2020 | De Jesus | ................ | G08B 3/10 |
| 11,226,243 B2 * | 1/2022 | Fujii | ................ | G01K 7/22 |
| 2002/0017997 A1 * | 2/2002 | Felkowitz | ................ | G01K 1/024 |
| | | | | 374/E1.004 |
| 2016/0202127 A1 * | 7/2016 | Chong | ................ | G01J 5/0859 |
| | | | | 374/121 |
| 2016/0278011 A1 | 9/2016 | Tomida | | |

FOREIGN PATENT DOCUMENTS

| | | | |
|---|---|---|---|
| KR | 10-1576147 B1 | | 12/2015 |
| KR | 10-2016-0005066 A | | 1/2016 |
| KR | 10-2017-0142701 A | | 12/2017 |
| KR | 20170142701 A | * | 12/2017 |
| KR | 20190033753 A | * | 4/2019 |

* cited by examiner

SMART THERMOMETER AND METHOD FOR MEASURING BODY TEMPERATURE USING THE SAME

BACKGROUND OF THE DISCLOSURE

Field of the Disclosure

The present disclosure relates to a smart thermometer, and more particularly, to a smart thermometer that provides an alarm for abnormal body temperature and continuous body temperature management, as well as body temperature measurement, by connecting an application in a smart device to the smart thermometer, and a method for measuring body temperature using the same.

Related Art

In recent years, various infectious respiratory diseases such as COVID-19 have been causing a pandemic. One of the most common symptoms of these infectious diseases is fever. Therefore, it is essential to measure body temperature to check for infection. For this reason, thermometers are becoming more and more common in the home and businesses, as well as medical facilities, for each individual's healthcare.

Moreover, thermometers are essential if you have a baby or toddler or if you are tracking your fertility cycle by measuring basal body temperature readings. In this regard, thermometers are increasingly used to measure body temperature accurately, check for any unusual changes to your body based on body temperature readings, and manage your health through a record of readings.

However, even if someone measures body temperature in the home on a continuous basis, it may be difficult to accurately track each individual's health by their body temperature unless their body temperature readings are recorded and managed on a regular basis. Thus, in the related art, there arises a need for a technology that can solve the above problems.

In relation to this, Korean Laid-Open Patent Publication No. 10-2014-0116579 (published on Oct. 6, 2014) titled "A smart body temperature management method using a Bluetooth-based mobile device-connected thermometer" discloses a technology that checks on body temperature readings taken from a thermometer on a mobile device by connecting the thermometer and the mobile device. However, this method only measures and records body temperature and is, therefore, of little help when it comes to health care using various information on the surroundings and body temperatures.

Meanwhile, Korean Patent Registration No. 10-1576147 (registered on Dec. 3, 2015) titled "A combined thermometer system using a smart device" proposes a technology that makes up for the above drawback that provides emergency measures for abnormal body temperature, as well as body temperature measurement, by connecting a thermometer and an application in a smart device. However, this conventional art technology requires the user to deal with the inconvenience of measuring their body temperature themselves on a regular basis.

Hence, this technical field now requires a technology that provides an alarm for abnormal body temperature and continuous body temperature management, as well as body temperature measurement, by connecting a smart thermometer and an application in a smart device.

PRIOR ART DOCUMENTS

Patent Documents

Korean Laid-Open Patent Publication No. 10-2014-0116579 (published on Oct. 6, 2014) titled "A smart body temperature management method using a Bluetooth-based mobile device-connected thermometer"

Korean Patent Registration No. 10-1576147 (registered on Dec. 3, 2015) titled "A combined thermometer system using a smart device"

SUMMARY OF THE DISCLOSURE

A technical aspect of the present disclosure is to provide a smart thermometer that provides an alarm for abnormal body temperature, as well as body temperature measurement, by connecting an application in a smart device to the smart thermometer, and a method for measuring body temperature using the same.

Another technical aspect of the present disclosure is to provide a smart thermometer that provides continuous monitoring and management of body temperature and a method for measuring body temperature using the same.

An exemplary embodiment of the present disclosure provides a method for measuring body temperature using a smart thermometer, the method comprising: performing advertising in idle mode; switching the smart thermometer to active mode and connecting to user equipment; measuring body temperature by using a temperature sensor; determining whether the measured body temperature stays below a first threshold for a preset period of time; if the measured body temperature stays below the first threshold for a preset period of time, switching to idle mode and performing advertising; and if the measured body temperature reaches or exceeds the first threshold within the preset period of time, displaying the measured body temperature on a display window and transmitting the measured body temperature to the user equipment.

The method may further comprise determining whether the measured body temperature is higher than a second threshold, and, if the measured body temperature is higher than the second threshold, triggering an alert sound.

When the user presses a wake-up button in idle mode, the smart thermometer may switch to active mode and connect to the user equipment.

When the user presses a wake-up button in active mode, the smart thermometer may switch to idle mode and perform advertising.

In the measuring of body temperature by using a temperature sensor, errors in body temperature readings taken by the temperature sensor may be corrected, based on error correction values stored in a memory which differ depending on the type of the temperature sensor and the area where the body temperature is measured.

Another exemplary embodiment of the present disclosure provides a smart thermometer comprising: a processor that switches the smart thermometer to active mode, measures body temperature by using a temperature sensor, determines whether the measured body temperature stays below a first threshold for a preset period of time, switches to idle mode and performs advertising, if the measured body temperature stays below the first threshold for a preset period of time, and displays the measured body temperature on a display window if the measured body temperature reaches or exceeds the first threshold within the preset period of time; and a communication part that performs advertising in idle mode, connects to user equipment in active mode, and transmits the measured body temperature to the user equipment.

The processor may determine whether the measured body temperature is higher than a second threshold, and, if the measured body temperature is higher than the second threshold, may trigger an alert sound.

When the user presses a wake-up button in idle mode, the processor may switch to active mode and connect to the user equipment.

When the user presses a wake-up button in active mode, the processor may switch to idle mode and perform advertising.

The processor may correct errors in body temperature readings taken by the temperature sensor, based on error correction values stored in a memory which differ depending on the type of the temperature sensor and the area where the body temperature is measured.

Yet another exemplary embodiment of the present disclosure provides an operation method for user equipment communicating with a smart thermometer, the method comprising: receiving the name of an antipyretic from a user; finding information on the dosage of the antipyretic from a database server or a memory provided in the user equipment; setting regular reminders based on the information on the dosage of the antipyretic; receiving body temperature data from the smart thermometer; determining whether the received body temperature reading is normal body temperature; if the received body temperature reading is not normal body temperature, determining whether it's time to take the antipyretic according to the regular reminder settings and sending a push notification telling the user to take the antipyretic; and if the received body temperature reading is normal body temperature, sending a push notification message telling the user to stop taking the antipyretic and disabling the regular reminders.

The method may further comprises if the received body temperature is not normal body temperature, searching for a related medical care facilities within a specified distance based on the current location determined by a GPS (Global Positioning System) and transmitting the body temperature data to the corresponding medical staff server.

DESCRIPTION OF EXEMPLARY EMBODIMENTS

Embodiments of the present disclosure will be described in detail below with reference to the accompanying drawings so that those having ordinary knowledge in the art to which the present disclosure pertains can easily practice the present invention. However, the present disclosure may be implemented in various different forms, and is not limited to the embodiments described herein. Throughout the specification, like parts are denoted by like reference numerals.

Throughout the specification, when a certain portion "includes" or "comprises" a certain component, this indicates that other components are not excluded and may be further included unless otherwise noted.

Figure 1:
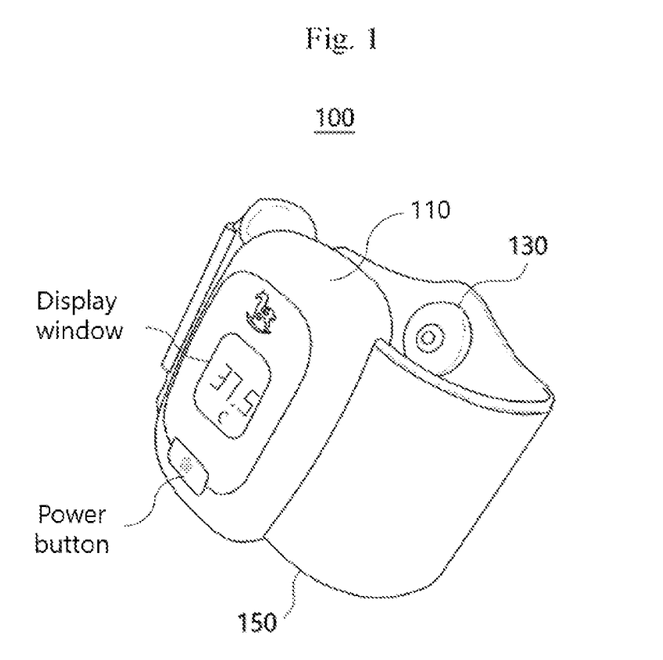
FIG. 1 is a perspective view showing an external configuration of a smart thermometer according to an exemplary embodiment of the present disclosure.

FIG. 1 is a perspective view showing an external configuration of a smart thermometer according to an exemplary embodiment of the present disclosure.

Referring to FIG. 1, a smart thermometer 100 according to an exemplary embodiment of the present disclosure comprises a main body 110, a temperature sensor 130, and a band portion 150.

Although not identified in the drawing by reference designation, the main body 110 comprises a power button and a display window. The power button allows for measuring body temperature, displaying body temperature readings on the display window, and connecting to user equipment, by switching the smart thermometer from idle mode to active mode. Pressing the power button once more in active mode switches the smart thermometer 100 to idle mode.

The temperature sensor 130 measures body temperature. Referring to FIG. 1, the temperature sensor 130 is configured to protrude at the center so that the temperature sensor fits well in the center of the armpit, for precise temperature measurement. Also, the temperature sensor 130 may be a contact or contactless sensor, preferably, a heat conduction-type, contactless temperature sensor. The temperature sensor 130 may measure body temperature at intervals of a few seconds.

The band portion 150 fixes the smart thermometer 100 to the wearer's body. The band portion 150 may be made of permeable material, and the band portion 150, placed on either side of the main body 110, has a first Velcro fastening and a second Velcro fastening, and the smart thermometer 100 may be fixed to the wearer's body by the first Velcro fastening and second Velcro fastening held together. For example, the smart thermometer 100 may be fixed to the upper part of the arm so that the temperature sensor 130 attaches tightly under the armpit to measure body temperature.

Figure 2:
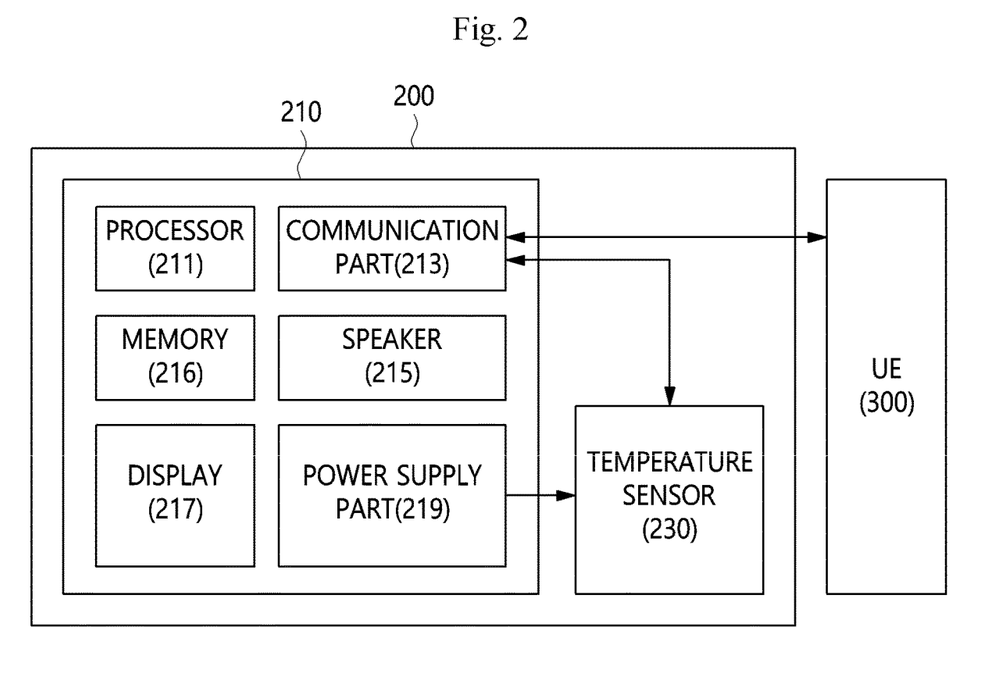
FIG. 2 is a block diagram showing an internal configuration of a smart thermometer according to an exemplary embodiment of the present disclosure.

FIG. 2 is a block diagram showing an internal configuration of a smart thermometer according to an exemplary embodiment of the present disclosure.

Referring to FIG. 2, a smart thermometer 200 according to an exemplary embodiment of the present disclosure comprises a main body 210 and a temperature sensor 230.

The main body 210 comprises a processor 211, a communication part 213, a speaker 215, a memory 216, a display 217, and a power supply part 219.

The processor 211 controls all operations related to the operation of the smart thermometer 200. For example, the processor 211 may activate the temperature sensor 230 to measure body temperature and store its readings in the memory 216. Also, the processor 211 may activate the communication part 213 to transmit body temperature data stored in the memory 216 to user equipment 300. The processor 211 may be a micro controller unit (MCU).

Moreover, the processor 211 increases the accuracy of body temperature measurement by correcting errors in body temperature readings taken by the temperature sensor 230. A server (not shown), the user equipment 300, or the memory 216 stores different error correction values depending on the type of the temperature sensor 230 and the area where the body temperature is measured, and corrects body temperature readings depending on the type of the temperature sensor 230 and depending on the area where the body temperature is to be measured. For example, if the temperature sensor 230 is a heat conduction-type temperature sensor, there may be an error of 2.4° C. when body temperature is taken under the armpit. In this case, the processor 211 may correct this error of 2.4° C. to get a more accurate body temperature reading.

The communication part 213 sends and receives, to and from the user equipment 300, body temperature data taken by the temperature sensor 230, battery information of the power supply part 210, and information related to the operation of the smart thermometer 200. The communication part 213 may include an NFC chip, an NFC antenna, a Bluetooth module, a Wi-Fi module, a 5G communication module, and so on. For example, the communication part 213 may communicate with the user equipment 300 via Bluetooth 4.0 communication.

When there is an unusual change in body temperature or the user's body temperature is out of a normal range, the speaker 215 triggers an alarm with a beep sound or the like. For example, the speaker 215 may be set to trigger an alarm every 30 minutes if the user's body temperature is above 37.7° C. and every 10 minutes if the user's body temperature is above 38.6° C. Also, the speaker 215 may trigger an alarm with a beep sound when connected to the user equipment 300 or disconnected from it. On the other hand, if the user's body temperature is below 33° C., this indicates that the smart thermometer is worn in a wrong position and the speaker 215 may trigger an alarm telling the user to check where on the body the user is wearing the smart thermometer.

The memory 216 stores user information, body temperature data, etc. of the smart thermometer 200.

The display 217 shows the user's body temperature data in real time. For example, the display 217 take measurements through the temperature sensor 230 and shows numeric values of body temperature readings corrected by the processor 211. The body temperature readings are available in both Celsius (° C.) and Fahrenheit (° F.).

The power supply part 219 supplies power required to activate the smart thermometer 200. The power supply part 219 may comprise a battery—for example, a CR2032 battery.

The temperature sensor 230 measures the user's body temperature. The temperature sensor 230 may be a contact or contactless thermometer—for example, a heat conduction-type thermometer.

Figure 3:
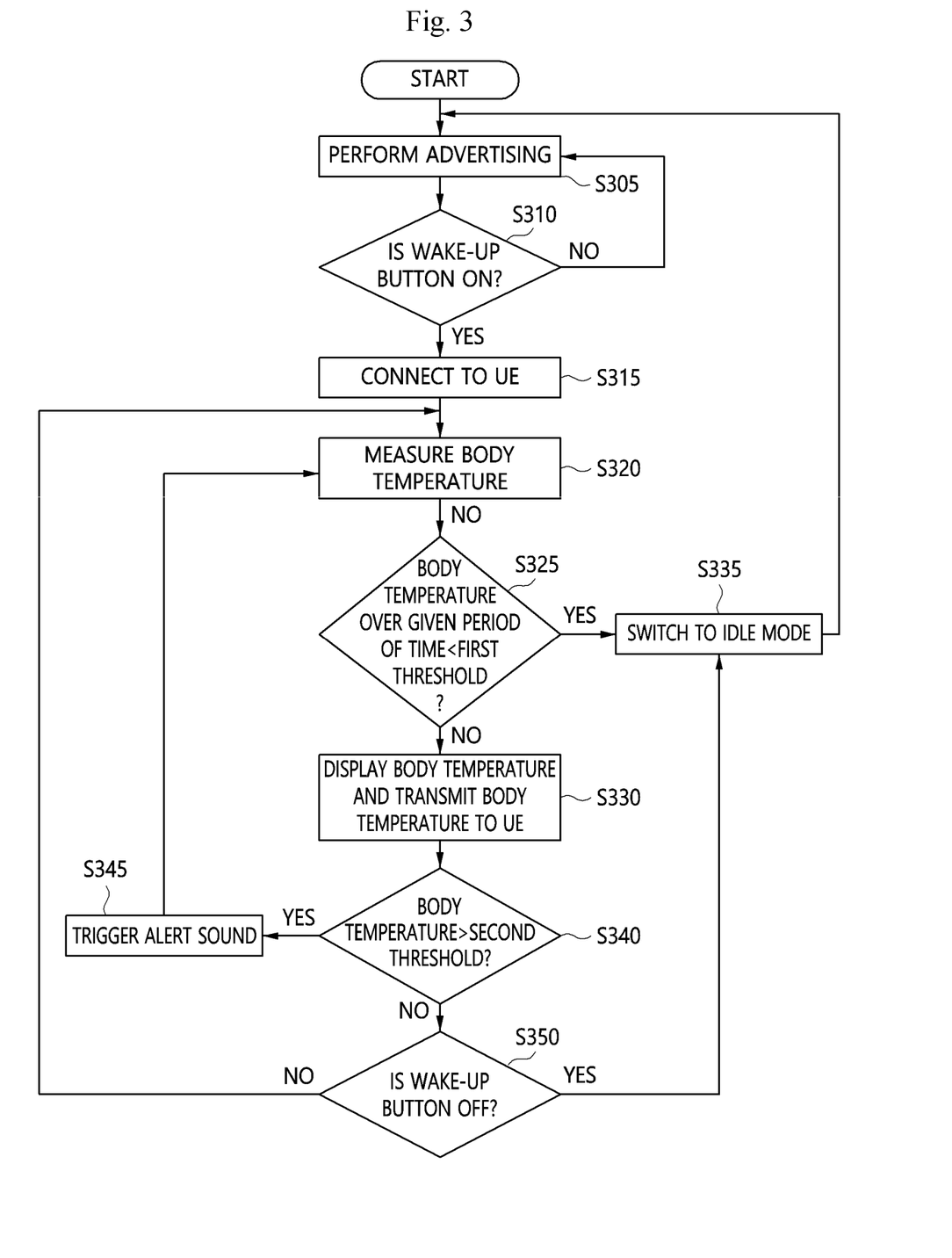
FIG. 3 is a flowchart showing a method of operating a smart thermometer according to an exemplary embodiment of the present disclosure.

FIG. 3 is a flowchart showing a method of operating a smart thermometer according to an exemplary embodiment of the present disclosure.

Referring to FIG. 3, a smart thermometer performs advertising in idle mode (S305). The reason why advertising is performed at this point is to minimize delay time taken to connect to user equipment.

Next, the smart thermometer checks whether a wake-up button is on (S310), and, if the wake-up button is on, connects to the user equipment (S315). At this point, if the user presses the wake-up button once in idle mode, the smart thermometer may switch to active mode in response to the pressing motion and perform the following operations related to body temperature measurement. Also, if the user presses the wake-up button once in active mode, the smart thermometer may switch back to idle mode in response to the pressing motion and perform advertising (S305). In the present disclosure, the smart thermometer in idle mode means that the wake-up button is off, and that the smart thermometer in active mode means that the wake-up button is on. Thus, the step S315 may be performed when the smart thermometer switches to active mode.

In this case, the smart thermometer may connect to the user equipment via Bluetooth communication.

Next, the smart thermometer measures body temperature by using a temperature sensor (S320). In this instance, the smart thermometer may increase the accuracy of body temperature measurement by correcting errors in body temperature readings taken by the temperature sensor, based on error correction values stored in a memory which differ depending on the type of the temperature sensor and the area where the body temperature is measured. For example, the temperature sensor may be a heat conduction-type temperature sensor, and there may be an error of 2.4° C. when body temperature is taken under the armpit. In this case, the smart thermometer may correct this error of 2.4° C. to give a more accurate body temperature reading. The smart thermometer may obtain the error correction values from the user equipment or an external server.

Next, the smart thermometer determines whether the measured body temperature stays below a first threshold for a preset period of time (S325). If the measured body temperature stays below the first threshold for a preset period of time, the smart thermometer then switches to idle mode (S335) and performs advertising (S305). For example, the preset period of time may be 3 minutes, and the first threshold may be set to 33° C. In this case, if the body temperature is measured for 3 minutes and stays below 33° C., the smart thermometer then switches to idle mode and performs advertising.

Meanwhile, if the measured body temperature reaches or exceeds the first threshold within the preset period of time, the smart thermometer then displays the measured body temperature on a display window and transmits it to the user equipment (S330).

Next, the smart thermometer determines whether the measured body temperature is higher than a second threshold (S340). If the measured body temperature is higher than the second threshold, then the smart thermometer triggers an alert sound (S345), and repeats the steps of measuring body temperature, comparing the measured body temperature with the first and second thresholds, displaying the body temperature reading, and transmits it to the user equipment. For example, if the second threshold is set to 37.7° C. and the measured body temperature is higher than 37.7° C., the smart thermometer then may trigger an alert sound (S345) and repeat the operations of the steps S320 to S340.

Meanwhile, if the result of the determination in S340 shows that the measured body temperature is at or below the second threshold, the smart thermometer checks whether the wake-up button is off (S350). If the wake-up button is off, the smart thermometer switches to idle mode (S335) and performs advertising (S305). On the contrary, if the wake-up button is on, the smart thermometer continues to measure body temperature (S320).

With this operation, if there is no temperature reading taken from the smart thermometer that is at or above the thresholds for a period of time, it is considered that the user's body temperature is not being taken at the moment and the smart thermometer may automatically switch to idle mode. Thus, unnecessary power consumption can be avoided. Also, when it is considered that the user's body temperature is not being taken at the moment, no temperature readings are shown on the display window, and no body temperature data is transmitted to the user equipment, thereby avoiding unnecessary power consumption.

Figure 4:
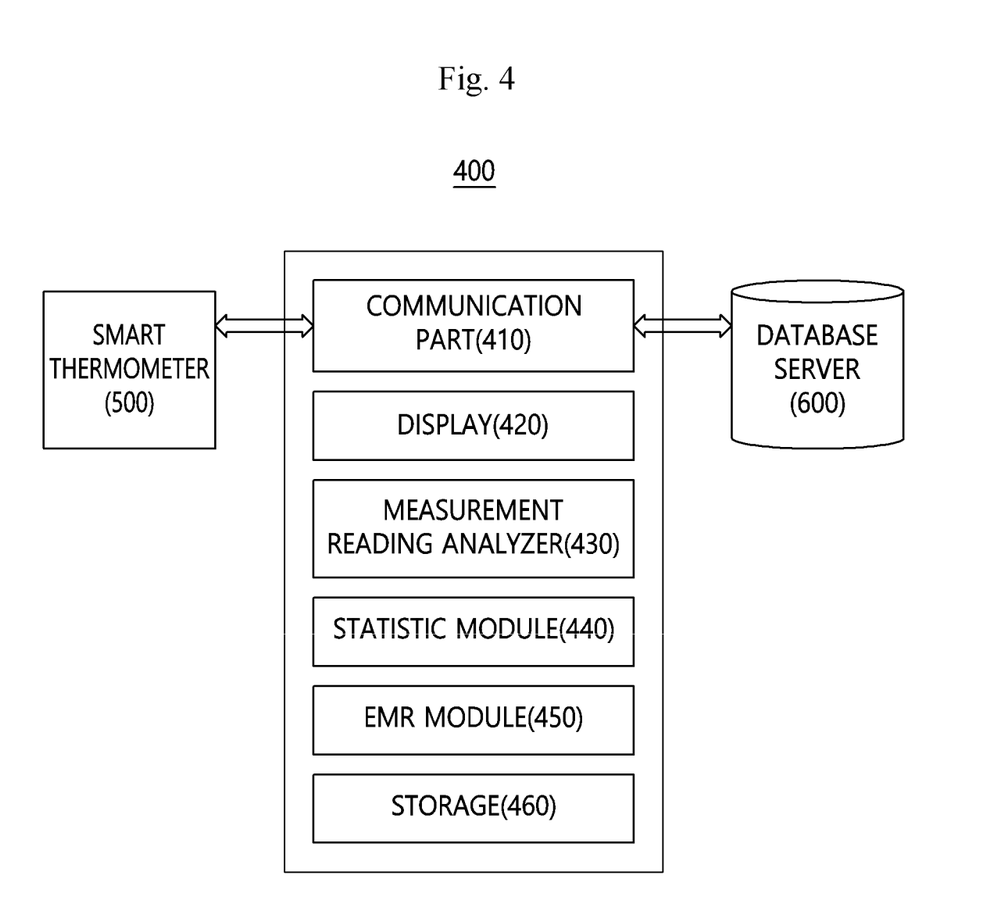
FIG. 4 is a block diagram showing an internal configuration of user equipment according to an exemplary embodiment of the present disclosure.

FIG. 4 is a block diagram showing an internal configuration of user equipment according to an exemplary embodiment of the present disclosure. The user equipment may be a user device capable of wireless communication, such as a smartphone, a tablet PC, and a laptop.

Referring to FIG. 4, user equipment 400 comprises a communication part 410, a display 420, a measurement reading analyzer 430, a statistic module 440, an EMR module 450, and a storage 460.

The communication part 410 sends and receives, to and from a smart thermometer 500, body temperature data and information related to the operation of the smart thermometer 500. The communication part 410 may include an NFC chip, an NFC antenna, a Bluetooth module, a Wi-Fi module, a 5G communication module, and so on. For example, the communication part 410 may communicate with the smart thermometer 500 via Bluetooth 4.0 communication.

The display 420 shows numeric values of body temperature readings taken by the smart thermometer 500.

The measurement reading analyzer 430 shows what the user's body temperature reading indicates. For example, the measurement reading analyzer 430 takes information such as gender and birthdate from the user in advance, compares the user's body temperature to the normal body temperature range for the user's age stored in a database server 600, and considers the user's body temperature "normal body temperature" when it is within the normal body temperature range. When the user's body temperature is out of the stored normal body temperature range for their age, it is considered "high" or "low". To determine what the user's body temperature reading indicates, a phrase "normal body temperature", "high", or "low" may be shown on the screen through the display 420. Meanwhile, the user equipment 400 may set a different background color for the screen of the display 420 depending on what the measurement reading analyzer 430 considers the body temperature reading to be. For example, the background of the screen may be shown in red if the user's body temperature is high and in blue if the user's body temperature is low. If the user's body temperature is normal, the background of the screen may be shown in green.

The statistic module 440 shows multiple body temperature readings taken at regular time intervals in a statistical graph including lines, surfaces, and solids. In an example, the user's body temperature readings taken at 3:00, 3:30, 4:00, and 4:30 on May 5 are connected in a line and plotted on a graph. Also, the statistical module 440 provides a healthcare schedule, including a statistical graph of the user's body temperature readings, an antipyretic medication history, and the dates of visits to a doctor. In an example, the statistical module 440 provides a healthcare schedule that lets the user to see a statistical graph of their body temperature readings, the dates of visits to a doctor, etc. on a monthly basis.

If it is considered that the user's body temperature reading is out of the stored normal body temperature range for their age and that the user needs medical help, the EMR (electronic medical record) module 450 finds nearby medical care facilities within a specified distance based on the current location determined by a GPS (not shown) and sends the body temperature data to their servers. At this point, telemedicine may be conducted if required. In this case, telemedicine is provided over video conference by using an image-capture device mounted inside the user equipment 400.

Moreover, the EMR module 450 may manage the user's antipyretic medication history. For example, the EMR module 450 may receive the name of an antipyretic the user is taking from the user and find information on the time intervals between doses, the amount of dose, and the number of doses from the database server 600 or storage 460. In this case, the EMR module 450 may provide reminders to the user at the time intervals between doses of the antipyretic. For example, if the user needs to take the antipyretic every four hours, the EMR module 450 may send push notifications to the user every four hours.

The storage 460 stores information such as the user's gender, birthdate, etc., the body temperature readings received from the smart thermometer 500, and information on the antipyretic the user is taking, and so forth. In addition, the storage 460 may store information on the time intervals between doses, the amount of dose, and the number of doses.

Figure 5:
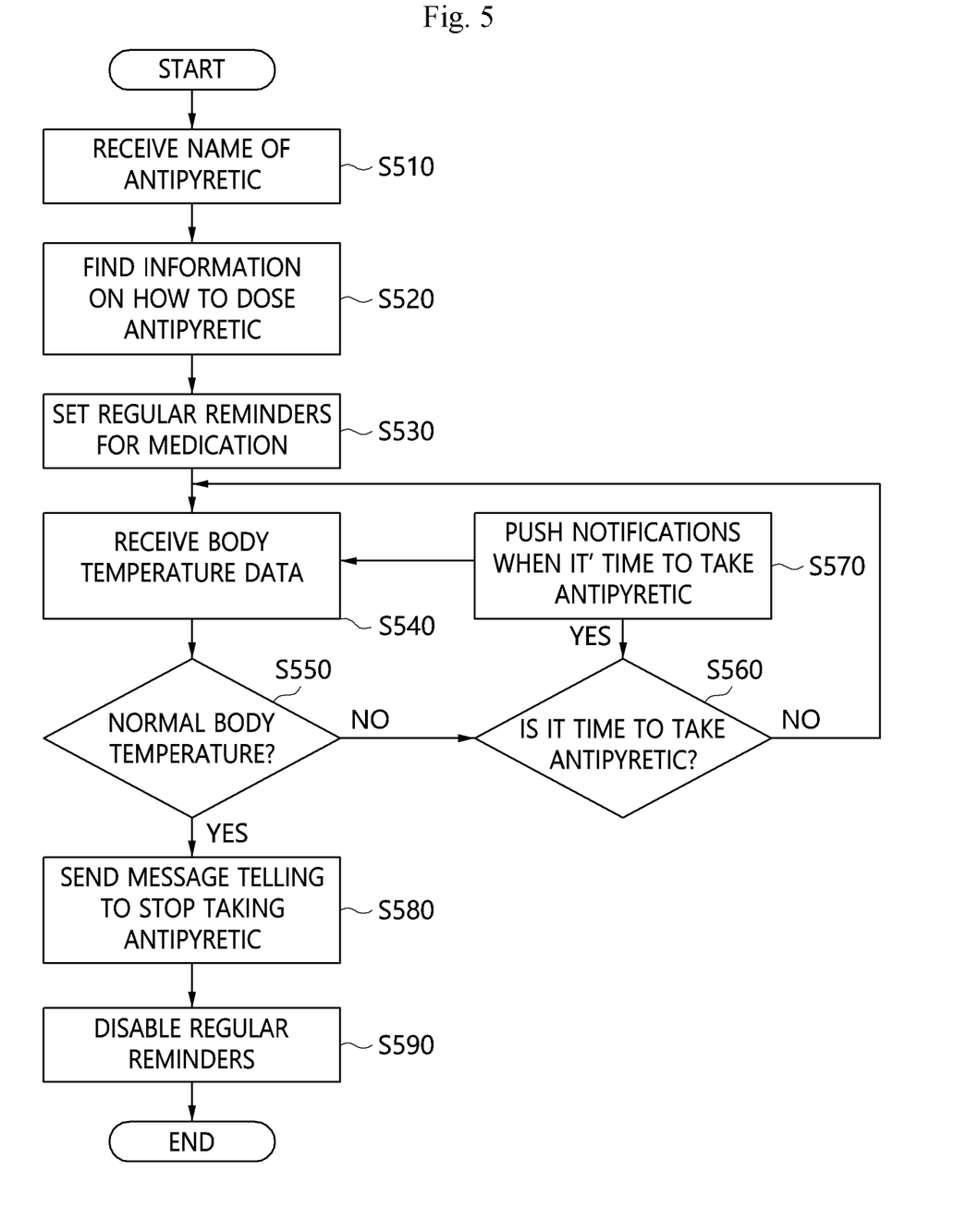
FIG. 5 is a flowchart showing a process showing how an antipyretic dosage reminder feature works on user equipment according to an exemplary embodiment of the present disclosure.

FIG. 5 is a flowchart showing a process showing how an antipyretic dosage reminder feature works on user equipment according to an exemplary embodiment of the present disclosure.

Referring to FIG. 5, user equipment receives the name of an antipyretic the user is taking from the user (S510).

Next, the user equipment finds information on the dosage of the antipyretic whose name is provided by the user in the step S510 from a database server or a memory provided in the user equipment (S520), and sets regular reminders for the dosage of the antipyretic based on information such as the user's gender, birthdate, etc. and the information on the dosage of the antipyretic (S530). For example, if the antipyretic whose name is provided by the user in the step S510 requires the user to take it every four hours, the user equipment sets reminders to be sent to the user every four hours.

Next, the user equipment receives the user's body temperature data from a smart thermometer (S540), and determines whether the body temperature reading received from the smart thermometer is normal body temperature (S550). If the received body temperature reading is normal body temperature, the user equipment sends a push notification message telling the user to stop taking the antipyretic (S580), and disables the regular reminders set in the step S530 (S590).

Meanwhile, if the result of the determination in the step S550 shows that the received body temperature reading is not normal body temperature, the user equipment determines whether it's time to take the antipyretic (S560). If it's time to take the antipyretic, the user equipment sends a push notification telling the user to take the antipyretic (S570), and continues to receive the user's body temperature data from the smart thermometer (S540). On the contrary, if it's not time to take the antipyretic, the user equipment continues to receive the user's body temperature data from the smart thermometer without sending a push notification (S540).

Meanwhile, although not shown in the drawing, if it is considered that the user's body temperature reading is out of the stored normal body temperature range for their age and that the user needs medical help, the UE finds nearby medical care facilities within a specified distance based on the current location determined by a GPS (not shown) and sends the body temperature data to their servers.

Figure 6:
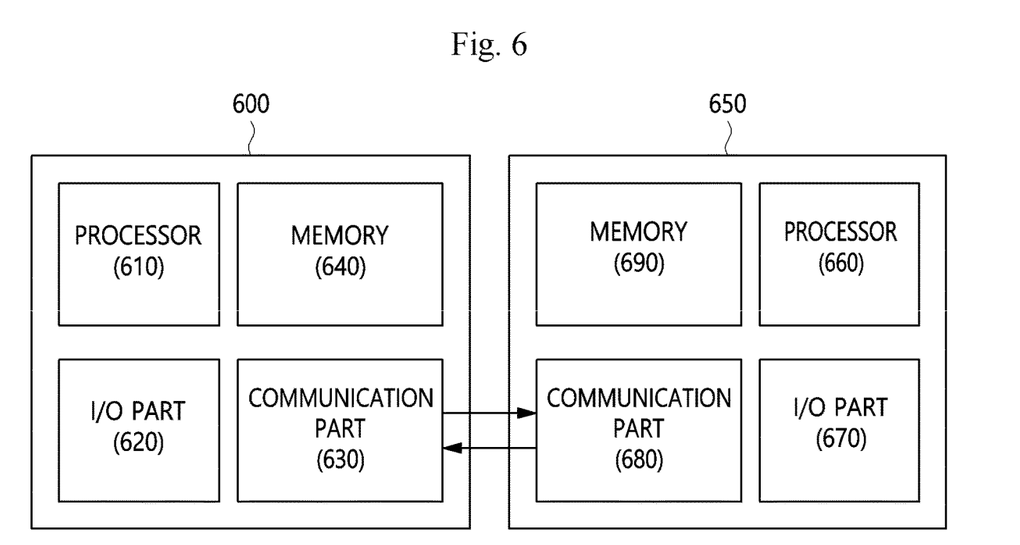
FIG. 6 is a block diagram showing a schematic configuration of a smart thermometer system according to an exemplary embodiment of the present disclosure.

FIG. 6 is a block diagram showing a schematic configuration of a smart thermometer system according to an exemplary embodiment of the present disclosure.

Referring to FIG. 6, a smart thermometer system according to an exemplary embodiment of the present disclosure comprises a smart thermometer 600 and a user equipment 650.

The smart thermometer 600 comprises a processor 610, an input/output part 620, a communication part 630, and a memory 640. The communication part 630 communicates with the user equipment 650.

The processor 610 implements the temperature measurement process and/or method proposed in the present disclosure. More specifically, the processor 610 implements all operations of the smart thermometer explained in the embodiments disclosed in the present disclosure, and performs the operation of the smart thermometer as in FIG. 3.

For example, the processor 610 may perform advertising in idle mode. The reason why advertising is performed at this point is to minimize delay time taken to connect to user equipment.

Moreover, the processor 610 checks whether a wake-up button is on, and, if the wake-up button is on, connects to the user equipment. At this point, the smart thermometer may connect to the user equipment via Bluetooth communication.

In addition, the processor 610 measures body temperature by using a temperature sensor. At this point, the processor 610 may increase the accuracy of body temperature measurement by correcting errors in body temperature readings taken by the temperature sensor. For example, the temperature sensor may be a heat conduction-type temperature sensor, and there may be an error of 2.4° C. when body temperature is taken under the armpit. In this case, the processor 610 may correct this error of 2.4° C. to give a more accurate body temperature reading. Meanwhile, the processor 610 may obtain error correction values from a server, the user equipment, or the memory of the smart thermometer.

Furthermore, the processor 610 determines whether the measured body temperature stays below a first threshold for a preset period of time. If the measured body temperature stays below the first threshold for a preset period of time, the processor 610 then switches to idle mode and performs advertising. For example, the preset period of time may be 3 minutes, and the first threshold may be set to 33° C. In this case, if the body temperature is measured for 3 minutes and stays below 33° C., the processor 610 then switches to idle mode and performs advertising.

Furthermore, if the measured body temperature reaches or exceeds the first threshold within the preset period of time, the processor 610 then displays the body temperature on a display window and transmits it to the user equipment.

Next, the processor 610 determines whether the measured body temperature is higher than a second threshold. If the measured body temperature is higher than the second threshold, then the processor 610 triggers an alert sound and repeatedly measures body temperature. For example, if the second threshold is set to 37.7° C. and the measured body temperature is higher than 37.7° C., the processor 610 then may trigger an alert sound and repeatedly measure body temperature.

Meanwhile, if the result of the comparison between the measured body temperature and the second threshold shows that the measured body temperature is at or below the second threshold, the processor 610 checks whether the wake-up button is off. If the wake-up button is off, the processor 610 switches to idle mode and performs advertising. On the contrary, if the wake-up button is on, the processor 610 continues to measure body temperature.

The input/output part 620 is connected to the processor 610 and sends and/or receives body temperature readings. For example, the input/output part 620 may display numeric values of body temperature readings through a display window, and may give out a beep sound when a body temperature reading is out of range.

The communication part 630 is connected to the processor 610 and sends and/or receives information to and from the user equipment 650. For example, the communication part 630 may receive information on the time intervals of body temperature measurement or temperature scales (Fahrenheit and Celsius) shown on the display window. On the contrary, the communication part 630 may send to the user equipment 650 information on body temperature readings and remaining battery level information.

The memory 640 may be various types of volatile or non-volatile storage media. In this case, the memory 640 may store at least any of information related to the operation of the smart thermometer, such as information on body temperature readings, information on remaining battery level, and the time intervals of body temperature measurement.

The user equipment 650 comprises a processor 660, an input/output part 670, a communication part 680, and a memory 690. The communication part 680 may communicate with the smart thermometer 600 or a server (not shown).

The processor 610 implements the operation process and/or method for user equipment proposed in the present disclosure. More specifically, the processor 610 implements all operations of the user equipment explained in the embodiments disclosed in the present disclosure, and performs the operation of the user equipment as in FIG. 5.

For example, the processor 660 may receive the name of an antipyretic the user is taking from the user.

Moreover, the processor 660 may find information on the dosage of the antipyretic whose name is provided by the user from a database server, and sets regular reminders for the dosage of the antipyretic based on stored information such as the user's gender, birthdate, etc. and the information on the dosage of the antipyretic. For example, if the antipyretic whose name is provided by the user requires the user to take it every four hours, the processor 660 may set reminders to be sent to the user every four hours.

In addition, the processor 660 receives the user's body temperature data from a smart thermometer, and determines whether the body temperature reading received from the smart thermometer is normal body temperature. If the received body temperature reading is normal body temperature, the processor 660 sends a push notification message telling the user to stop taking the antipyretic, and disables the regular reminders.

Meanwhile, if the received body temperature reading is not normal body temperature, the processor 660 determines whether it's time to take the antipyretic. If it's time to take the antipyretic, the processor 660 sends a push notification telling the user to take the antipyretic and continues to receive the user's body temperature data from the smart thermometer. On the contrary, if it's not time to take the antipyretic, the processor 660 continues to receive the user's body temperature data from the smart thermometer without sending a push notification.

As seen from above, a smart thermometer and a control method therefor according to the present disclosure are not limited by the configurations and methods of the foregoing embodiments, but all or some of the embodiments may be selectively combined to provide various modifications.

An advantage of the present disclosure is to provide an alarm for abnormal body temperature, as well as body temperature measurement, by connecting an application in a smart device to the smart thermometer.

Another advantage of the present disclosure is to provide a smart thermometer that provides continuous monitoring of body temperature and manages batteries efficiently.

What is claimed is:

1. A method for measuring body temperature using a smart thermometer, the method comprising:
    performing advertising in idle mode;
    switching the smart thermometer to active mode and connecting to user equipment;
    measuring body temperature of a user by using a temperature sensor that includes a measurement reading analyzer;
    determining whether the measured body temperature stays below a first threshold for a preset period of time;
    if the measured body temperature stays below the first threshold for the preset period of time, switching to idle mode and performing advertising; and
    if the measured body temperature reaches or exceeds the first threshold within the preset period of time, displaying the measured body temperature on a display window and transmitting the measured body temperature to the user equipment,
    wherein the measurement reading analyzer is configured to compare the measured body temperature of the user with a normal body temperature range determined according to user characteristics,
    wherein the display window includes a screen background and is configured to a display the screen background as a specific color based on the comparison, the screen background being displayed as a first color if the measured body temperature is high compared to the normal body temperature range, being displayed as a second color if the measured body temperature is low compared to the normal body temperature range, and being displayed as a third color if the measured body temperature falls in the normal body temperature range,
    wherein the smart thermometer includes a main body and a band portion disposed on either side of the main body,
    wherein the temperature sensor further includes a protruding portion this is centrally formed and is configured to fit the temperature sensor in the armpit,
    wherein the band portion includes a first Velcro fastening and a second Velcro fastening, the first Velcro fastening and the second Velcro fastening configured to attach the temperature sensor tightly under the armpit, and
    wherein the user equipment is configured to communicate with the smart thermometer by
        receiving, from the user, a name of an antipyretic the user is taking,
        finding information on a dosage of the antipyretic stored in a database server or a memory provided in the user equipment,
        setting regular reminders for the dosage of the antipyretic based on the user characteristics and the information on the dosage of the antipyretic,
        receiving body temperature data from the smart thermometer, and
        determining whether the received body temperature data indicates a body temperature reading that falls in the normal body temperature range,
    wherein the user equipment is further configured to determine whether it is time to take the antipyretic according to the regular reminder setting, if the body temperature reading does not fall in the normal body temperature range,
    wherein, if it is time to take the antipyretic, the user equipment sends a push notification telling the user to take the antipyretic and continues to receive the body temperature data from the smart thermometer, and
    wherein, if it is not time to take the antipyretic, the user equipment continues to receive the body temperature data from the smart thermometer without sending the push notification.

2. The method of claim 1, further comprising determining whether the measured body temperature is higher than a second threshold, and, if the measured body temperature is higher than the second threshold, triggering an alert sound.

3. The method of claim 1, wherein, when the user presses a power button in idle mode, the smart thermometer switches to active mode and connects to the user equipment.

4. The method of claim 1, wherein, when the user presses a power button in active mode, the smart thermometer switches to idle mode and performs advertising.

5. The method of claim 1, further comprising:
    correcting body temperature readings taken by the temperature sensor during the body temperature measuring, based on error correction values stored in a memory,
    wherein the error correction values differ depending on a type of the temperature sensor and an area where the body temperature is measured.

6. The method of claim 1,
    wherein the user characteristics are determined by providing information to the measurement reading analyzer, the information including the user's gender and the user's date of birth, and
    wherein the first color is red, the second color is blue, and the third color is green.

7. A smart thermometer comprising:
    a processor that switches the smart thermometer to active mode, measures body temperature of a user by using a temperature sensor that includes a measurement reading analyzer, determines whether the measured body temperature stays below a first threshold for a preset period of time, switches to idle mode and performs advertising if the measured body temperature stays below the first threshold for the preset period of time, and displays the measured body temperature on a display window if the measured body temperature reaches or exceeds the first threshold within the preset period of time; and
    a communication part that performs advertising in idle mode, connects to user equipment in active mode, and transmits the measured body temperature to the user equipment,
    wherein the measurement reading analyzer is configured to compare the measured body temperature of the user with a normal body temperature range determined according to user characteristics, and
    wherein the display window includes a screen background and is configured to a display the screen background as a specific color based on the comparison, the screen background being displayed as a first color if the measured body temperature is high compared to the normal body temperature range, being displayed as a second color if the measured body temperature is low compared to the normal body temperature range, and being displayed as a third color if the measured body temperature falls in the normal body temperature range, the smart thermometer further comprising a main body and a band portion disposed on either side of the main body, wherein the temperature sensor further includes a protruding portion this is centrally formed and is configured to fit the temperature sensor in the armpit, 36 wherein the band portion includes a first Velcro fastening and a second Velcro fastening, the first Velcro fastening and the second Velcro fastening configured to attach the temperature sensor tightly under the armpit, and wherein the user equipment is configured to communicate with the smart thermometer by receiving, from the user, a name of an antipyretic the user is taking, finding information on a dosage of the antipyretic stored in a database server or a memory provided in the user equipment, setting regular reminders for the dosage of the antipyretic based on the user characteristics and the information on the dosage of the antipyretic, receiving body temperature data from the smart thermometer, and determining whether the received body temperature data indicates a body temperature reading that falls in the normal body temperature range, wherein the user equipment is further configured to determine whether it is time to take the antipyretic according to the regular reminder setting, if the body temperature reading does not fall in the normal body temperature range, wherein, if it is time to take the antipyretic, the user equipment sends a push notification telling the user to take the antipyretic and continues to receive the body temperature data from the smart thermometer, and wherein, if it is not time to take the antipyretic, the user equipment continues to receive the body temperature data from the smart thermometer without sending the push notification.

8. The smart thermometer of claim 7, wherein the processor determines whether the measured body temperature is higher than a second threshold, and, if the measured body temperature is higher than the second threshold, triggers an alert sound.

9. The smart thermometer of claim 7, wherein, when the user presses a power button in idle mode, the processor switches to active mode and connects to the user equipment.

10. The smart thermometer of claim 7, wherein, when the user presses a power button in active mode, the processor switches to idle mode and performs advertising.

11. The smart thermometer of claim 7, wherein the processor corrects body temperature readings taken by the temperature sensor during the body temperature measuring, based on error correction values stored in a memory, and wherein the error correction values differ depending on a type of the temperature sensor and an area where the body temperature is measured.

12. The smart thermometer of claim 7, wherein the user characteristics are determined by providing information to the measurement reading analyzer, the information including the user's gender and the user's date of birth, and wherein the first color is red, the second color is blue, and the third color is green.

* * * * *